United States Patent [19]

Tóth et al.

[11] Patent Number: 5,132,309

[45] Date of Patent: * Jul. 21, 1992

[54] 2-OXO-3,8-DIAZASPIRO(4,5)DECANE DERIVATIVES, PHARMACEUTICAL COMPOSITIONS CONTAINING THEM AND PROCESS FOR PREPARING SAME

[75] Inventors: Edit Tóth; József Törley; Sándor Görög; László Szporny; Béla Kiss; Éva Pálosi; Dóra Groó; István Laszlovszky; Erzsébet Lapis; Ferenc Auth; László Haál, all of Budapest, Hungary

[73] Assignee: Richter Gedeon Vegyeszeti Gyar RT, Budapest, Hungary

[*] Notice: The portion of the term of this patent subsequent to Jun. 2, 2009 has been disclaimed.

[21] Appl. No.: 566,279

[22] Filed: Aug. 10, 1990

[30] Foreign Application Priority Data

Aug. 10, 1989 [HU] Hungary ............................. 4094/89

[51] Int. Cl.$^5$ ..................... A61K 31/44; C07D 471/10
[52] U.S. Cl. ........................................ 514/278; 546/19
[58] Field of Search ............................ 546/19; 514/278

[56] References Cited

U.S. PATENT DOCUMENTS 3,399,192  8/1968  Regnier et al. ....................... 546/19

OTHER PUBLICATIONS

Jones, G. et al. "Substituted 1,1-Diphenyl. . ." J. Med. Chem. 14(2) 161-164 (1971).

Primary Examiner—Jane T. Fan
Assistant Examiner—Celia Chang
Attorney, Agent, or Firm—Herbert Dubno; Jonathan Myers

[57] ABSTRACT

The invention relates to, therapeutically active 2-oxo-3,8-diazaspiro[4,5]decane derivatives (I),

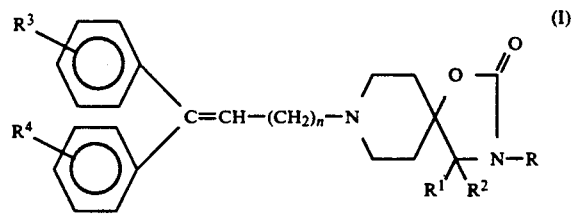

wherein
R means hydrogen, a $C_{1-12}$ alkyl, $C_{3-6}$ cycloalkyl, carbocyclic $C_{6-10}$ aryl or carbocyclic $C_{6-10}$ aryl-$C_{1-4}$ alkyl group, the latter two optionally being substituted on their aromatic moiety by one or more, same or different halogen(s) or one or more $C_{1-4}$ alkyl or $C_{1-4}$ alkoxy group(s);
one of $R^1$ and $R^2$ stands for a hydroxyl group whereas the other means a methyl gorup;
$R^3$ and $R^4$, which are the same or different, represent hydrogen, one or more halogen(s), $C_{1-4}$ alkyl, $C_{1-4}$ alkoxy, trihalomethyl group or a hydroxyl group optionally esterified by a $C_{1-4}$ alkanoic acid; and
n is 1 or 2, their isomers, solvates, hydrates, acid addition and quaternary ammonium salts.

9 Claims, No Drawings

2-OXO-3,8-DIAZASPIRO(4,5)DECANE DERIVATIVES, PHARMACEUTICAL COMPOSITIONS CONTAINING THEM AND PROCESS FOR PREPARING SAME

The invention relates to novel, therapeutically active 2-oxo-3,8-diazaspiro[4,5]decane derivatives of the formula (I),

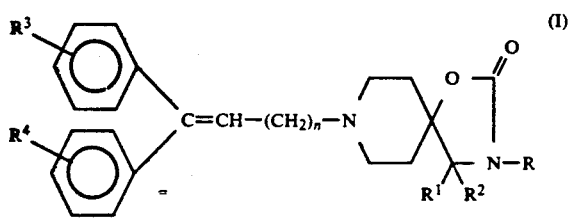

wherein
R means hydrogen, a $C_{1-12}$alkyl, $C_{3-6}$cycloalkyl, carbocyclic $C_{6-10}$aryl or carbocyclic $C_{6-10}$aryl-$C_{1-4}$alkyl group, the latter two optionally being substituted on their aromatic moiety by one or more, same or different halogen(s) or one or more $C_{1-4}$alkyl or $C_{1-4}$alkoxy group(s);
one of $R^1$ and $R^2$ stands for a hydroxyl group whereas the other means a methyl group;
$R^3$ and $R^4$, which are the same or different, represent hydrogen, one or more halogen(s), $C_{1-4}$alkyl, $C_{1-4}$alkoxy, trihalomethyl group or a hydroxyl group optionally esterified by a $C_{1-4}$alkanoic acid; and
n is 1 or 2,
their isomers, solvates, hydrates, acid addition and quaternary ammonium salts as well as pharmaceutical compositions containing these compounds.

The invention also relates to a process for the preparation of the above compounds and compositions as well as to a method of treatment. The latter comprises administering a therapeutically effective amount of a compound of the formula (I) or a pharmaceutically acceptable acid addition or quaternary ammonium salt thereof to a patient for influencing hypoxic, anoxic and ischaemic conditions.

The compounds of the formula (I) may exist in various stereoisomeric forms such as geometrical isomers as well as racemates, separated optical isomers or their mixtures, all of which may occur in the form of various solvates and hydrates. All these compounds and mixtures are within the scope of the invention.

A number of therapeutically useful 2-oxo-1-oxa-3,8-diazaspiro[4,5]decane derivatives have been described in the literature. Such compounds are reported e.g. in the following publications: C.A. 71, 91359d (1969); C.A. 78, 23876q (1973); C.A. 81, 33153c and 105368b (1974); C.A. 95, 161765e (1981); as well as in the DE patent specifications Nos. 2,013,729, 2,013,668 and 2,163,000 and in the BE patent specifications Nos. 775,984, 774,170, 786,631 and 825,444; in the GB patent specification No. 1,100,281; in the published NL patent specification No. 7,214,689; as well as in the U.S. Pat. Nos. 3,555,033, 3,594,386, 4,244,961 and 4,255,432.

A substantial difference between the compounds of formula (I) according to the invention and similar derivatives known up to the present appears in the nature of the substituents bound in position 4 and optionally in position 3 of the spirodecane skeleton.

According to an other aspect of the invention, there is provided a process for the preparation of the compounds of the formula (I) as well as their acid addition and quaternary ammonium salts, which comprises (a) reacting a 2-oxo-3,8-diazaspiro[4,5]decane derivative of the formula (II),

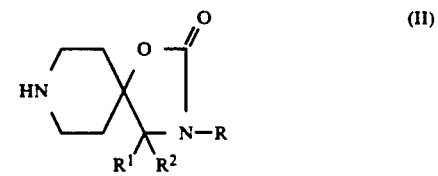

wherein R, $R^1$ and $R^2$ are as defined above, with a diphenylalkene derivative of the formula (III),

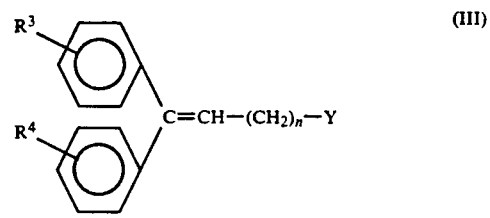

wherein $R^3$, $R^4$ and n are as defined above and Y means halogen or a $C_{1-4}$alkylsulfonyloxy or arylsulfonyloxy group; or (b) reacting a 4-acetyl-4-hydroxypiperidine derivative of the formula (VII),

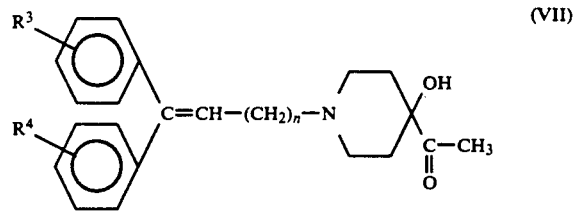

wherein $R^3$, $R^4$ and n are as defined above, with an isocyanate of the formula R-NCO, wherein R is as defined above, except hydrogen, and then cyclizing the thus-obtained 4-acetyl-4-carbamoyloxypiperidine derivative of the formula (VIII),

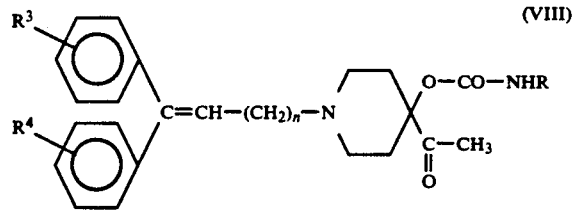

wherein R, $R^3$, $R^4$ and n are as defined above, or (c) cyclizing a 4-acetyl-4-carbamoyloxypiperidine derivative of the formula (VIII), wherein $R^3$, $R^4$ and n are as defined above and R is as defined for the formula R-NCO; or (d) reacting a compound of the formula (VI),

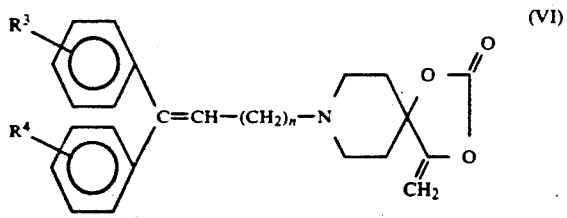

wherein $R^3$, $R^4$ and n are as defined above, with an amine of the formula $R-NH_2$, wherein R is as defined for the formula (I); or (e) hydrating a 4-methylene-2-oxo-3,8-diazaspiro[4,5]decane derivative of the formula (IV),

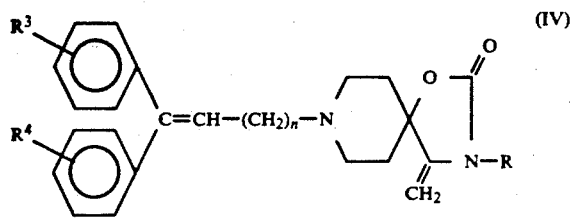

wherein R, $R^3$, $R^4$ and n are as defined above, in an acidic medium, then, if desired, transforming a functional group of a thus-obtained compound of the formula (I), wherein R, $R^1$, $R^2$, $R^3$, $R^4$ and n are as defined for the formula (I), to an other one in a known manner, and/or reacting a thus-obtained compound of the formula (I), wherein R, $R^1$, $R^2$, $R^3$, $R^4$ and n are as defined above, with an acid to give an acid addition salt and/or treating a compound of the formula (I), wherein R, $R^1$, $R^2$, $R^3$, $R^4$ and n are as defined above, obtained as a salt, with a base to liberate the free basic form thereof and/or converting a thus-obtained compound of the formula (I), wherein R, $R^1$, $R^2$, $R^3$, $R^4$ and n are as defined above, to its quaternary ammonium salt.

In the process (a) according to the invention a 2-oxo-3,8-diazaspiro[4,5]decane derivative of the formula (II) is brought into reaction with a diphenylalkene derivative of the formula (III), wherein Y means e.g. a mesyloxy or tosyloxy group or a halogen, preferably chlorine or bromine. This reaction is preferably accomplished in an inert organic solvent, in the presence of a base being capable of binding the acid liberated in the reaction. Suitable solvents are e.g. aliphatic alkanols such as ethanol, isopropanol or butanol; aromatic hydrocarbons such as chlorobenzene or toluene; ethers such as dibutyl ether or dioxane; tertiary aliphatic acid amides such as dimethylformamide or dimethylacetamide; ketones such as acetone, methyl ethyl ketone or methyl isobutyl ketone; but a mixture of the above solvents may be employed, too. For binding the acid liberated in the reaction, inorganic or tertiary organic bases, e.g. carbonates or hydrogen carbonates of alkaline metals or alkaline earth metals as well as organic bases, e.g. triethylamine, dimethylaniline or pyridine may be used; though an excess of the compound of the formula (II) is also suitable for this purpose. This reaction may be carried out between room temperature and the boiling point of the reaction mixture; optionally, a catalyst may also be added. Suitable catalysts are alkaline metal iodides. It is preferable to work under an inert gas such as nitrogen or argon.

In the case of process (b) according to the invention a 4-acetyl-4-hydroxypiperidine derivative of the formula (VII) is reacted with an isocyanate of the formula R-NCO, then the thus-formed 4-acetyl-4-carbamoyloxypiperidine derivative of the formula (VII) is cyclized. The condensation reaction according to the first step is carried out in a known manner (Houben-Weyl: Methoden der Organischen Chemie, Vol. VIII/3, page 137 to 147 (1952)). The 4-acetyl-4-carbamoyloxy-piperidine derivative thus-obtained is preferably cyclized in the presence of a base. Alkaline metal acetates, carbonates, alkoxides, hydroxides and/or tertiary organic bases, e.g. pyridine, tripropylamine or picoline, may be used as basic catalysts in the cyclization; the organic bases may also serve as solvents for the reaction. Further suitable solvents are e.g. aliphatic alcohols such as methanol, ethanol, propanol or butanol; aliphatic, alicyclic or aromatic hydrocarbons such as methylene chloride, hexane, cyclohexane, benzene, toluene or xylene; acid amides such as dimethylformamide or N-methylpyrrolidone; ethers such as dibutyl ether or dioxane; nitriles such as acetonitrile; sulfoxides, e.g. dimethyl sulfoxide; as well as mixtures of the above solvents. The reaction may be carried out without any solvent, too, e.g. in molten state. In order to accelerate the cyclization, the temperature is suitably increased: the reaction is preferably accomplished between 40° C. and the boiling point of the reaction mixture. It is suitable to work under an inert gas such as argon or nitrogen. According to a preferred embodiment, the 4-acetyl-4-carbamoyloxypiperidine derivative of the formula (VIII) obtained from the reaction of 4-acetyl-4-hydroxypiperidine derivative of the formula (VII) with the isocyanate of the formula R-NCO is not isolated but directly cyclized in the same reaction mixture in the presence of a suitable base.

In the case of process (c) of the invention the procedure described for the second step of process (b) is followed.

According to the process (d) of the invention a compound of the formula (VI) is reacted with an amine of the formula $R-NH_2$. This reaction may be carried out in a suitable solvent or without any solvent. Suitable solvents are e.g. aliphatic, alicyclic or araliphatic alcohols such as ethanol, butanol, cyclohexanol, benzyl alcohol; aliphatic or aromatic hydrocarbons such as hexane, heptane, xylene, chlorobenzene or nitrobenzene; ethers, e.g. dioxane or di-n-butyl ether; and tertiary organic bases, e.g. picoline, triethylamine or pyridine; though an excess of the amine of formula $R-NH_2$ may also serve as a solvent for the reaction. This procedure may be carried out at a temperature between room temperature and the boiling point of the reaction mixture, preferably under an inert gas, e.g. argon or nitrogen.

The hydration according to process(e) of the invention is performed in a medium containing water, in the presence of mineral and/or organic acids. Suitable acids are e.g. the hydrogen halides, sulfuric acid, phosphoric acid, formic acid, aromatic sulfonic acid, oxalic acid and the like. This reaction is preferably carried out at a temperature between 5° C. and the boiling point of the reaction mixture.

If desired, the compounds of the formula (I) obtained by using the processes (a) to (e) can be transformed in a known way to other compounds being within the scope of the scope of the formula (I).

If desired, the compounds of the formula (I) may be converted to the acid addition and quaternary ammonium salts by using know methods. For the preparation of acid addition salts inorganic or organic acids such as hydrogen halides, e.g. hydrochloric acid and hydrobromic acid; sulfuric acid, phosphoric acids as well as formic, acetic, propionic, oxalic, glycolic, maleic, fumaric, succinic, tartaric, ascorbic, citric, malic, salicylic, lactic, benzoic, cinnamic, aspartic, glutamic, N-acetyl-aspartic or N-acetylglutamic acid as well as alkanesulfonic acids such as methanesulfonic acid or arenesulfonic acids, e.g. p-toluenesulfonic acid and the like, may be used.

The salt formation can be carried out e.g. in such a way that the corresponding acid is added to the solution of the compound of the formula (I) prepared in an inert solvent, e.g. ethanol, thereafter the salt formed is precipitated by adding preferably a water-immiscible organic solvent, e.g. diethyl ether.

For the preparation of quaternary ammonium salts a lower alkyl, alkenyl or benzyl halide or an alkyl sulfate may preferably be employed. The quaternization is suitably performed in an organic solvent such as acetone, acetonitrile, ethanol or their mixtures at a temperature range from room temperature up to the boiling point of the solvent.

The acid addition or quaternary ammonium salt obtained may be isolated e.g. by filtration and, when necessary, purified by recrystallization.

Conversely, the corresponding free bases can be liberated from their salts by an alkaline treatment.

The starting substances used in the process of the invention are partly known or can be prepared by using known methods. The compounds of the formulae (VII) and (VIII) used as starting substances are novel and possess biological activity, too.

The compounds of the formula (III) may be prepared e.g. according to the following literature references: Ber. 55, 3406 (1922); Ann. Chem. 555, 80 (1952); GB patent specification No. 683,950; Yakugaku Zasshi 82, 1088 (1952); J. Chem. Soc. 4066 (1959); Coll. Czechoslov. Chem. Commun. 38, 3879 (1973).

The preparation of the compounds of the formula (II) is described in the Hungarian patent application No. 4092/89 and the concurrently filed commonly assigned copending U.S. application Ser. No. 566,274.

The compounds of the formula (IV) can be prepared by reacting 2-oxo-3,8-diazaspiro[4,5]decane derivatives of the formula (II), wherein $R^1$ and $R^2$ together represent a methylene group and R is as defined above, with diphenylalkene derivatives of the formula (III).

The carbamates of the formulae (V)

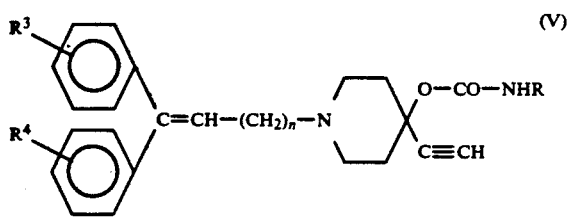

and (VIII) may be obtained e.g. by reacting a compound of the formula (IX),

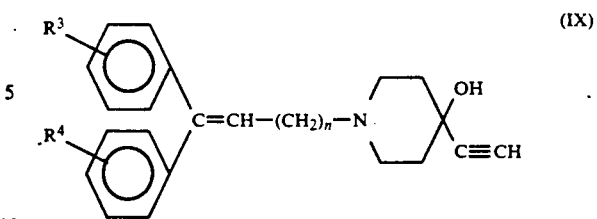

or (VII), respectively, with an isocyanate of the formula R-NCO as described hereinabove.

The compounds of the formula (VI) can be prepared by cyclizing a 4-carbamoyloxy-4-ethynylpiperidine derivative of the formula (V) in an acidic medium and then reacting the imino compound thus-obtained with water.

The 4-acetyl-4-hydroxypiperidine derivatives of the formula (VII) can be synthetized e.g. by hydrating a suitable 4-ethynyl-4-hydroxypiperidine derivative [see e.g.: Houben-Weyl: Methoden der Organischen Chemie, Vol. VII/2, pages 826 to 835 (1973)] or by the alkaline treatment of a suitable 4-methylene-2-oxo-1,3-dioxa-8-azaspiro[4,5]decane derivative of the formula (VI).

The compounds of the formula (IX) can be prepared e.g. by the ethynylation reaction of suitably substituted 4-piperidone derivatives as described e.g. in the Hungarian patent specification No. 166,769 or in Farmaco (Pavia) Ed. Sci. 12, 34 (1957).

The novel compounds of the formula (I) according to the invention and their salts possess valuable pharmacological properties: they exert e.g. a selective dopaminergic action in the central nervous system and show antihypoxic, antianoxic, antiischaemic and antiamnesic properties. Due to their dopaminergic effect, they inhibit the central dopamine (hereinafter: DA) receptors in the cortical and subcortical brain regions. They are capable of protecting against primary lessions caused by the cerebral hypoxia/ischaemia of various origin, e.g. the cerebral edema, memory damages induced by hypoxia and of prolonging the survival of mammals under severe hypoxic conditions. The compounds of the formula (I) can widely be used in the therapy for the prevention and treatment of various diseases such as mania, agitations of various origin, psychomotor disquiet, hyperkinesia, senile and multiinfarctual dementia, Alzheimer's disease, disturbances of the cognitive functions, ischaemic injuries and the like.

The pharmacological effects of the novel compounds of the formula (I) according to the invention were studied by using the methods described hereinafter.

1. Inhibition of the apomorhine-induced locomotor hyperactivity and stereotypy

Apomorphine induces a characteristic syndrome in rats and various animal species which manifests itself in the hyperactivity and stereotypic behavior of the animals [J. Pharm. Pharmacol. 19 627 (1957); J. Neurol. Transm. 40, 97 (1977); J. Psychiat. Res. 11, 1 (1974); J. Pharm. Pharmacol. 25, 1003 (1973); as well as Nature 263, 338 (1976)].

Male Hannover-Wistar rats weighing 160 to 180 g were used in these examinations. The test compounds were suspended in a 2% Tween 80 solution and diluted to the desired concentration by adding distilled water. The corresponding dose was administered to rats in a volume of 5 ml/kg. The control group was treated with the above solution containing no test substance.

One hour following the treatment with 2.5 mg/kg oral dose of the test compound, the rats were subcutaneously treated with 1 mg/kg of apomorphine hydrochloride.

At 15 minutes after administration of apomorphine, the animals were placed in a 5-channel behavior-observing device controlled by a microprocessor and the coordinated and stereotypic motion of the animals were measured for 15 minutes. Chlozapine (chemically 8-chloro-11-(4-methyl-1-piperazinyl)-5H-dibenzo[b,e][1,4]diazepine) was used in a dose of 2.5 mg/kg as reference drug. The results are given as percentages of the control for both motion types.

Further on, the cataleptogenic (catalepsy-inducing) effect of the compounds was investigated by using the method of G. Stille and H. Launer (Arzneim.-Forsch. 21, 252 (1971). In these examinations male Wistar rats weighing 90 to 110 g were used which were orally treated by various doses of the test substances. The number of cataleptic animals was hourly registered for 6 hours following the treatment. An animal was considered to be cataleptic when it did not correct within 30 seconds its whimsical body position caused by lifting its upper limbs onto a horizontal rod set at a height of 8 cm. The $ED_{50}$ value was calculated from the percentage of cataleptic animals. The results are summarized in Table 1.

The abbreviations used in the Table are as follows:
LMA: locomotor activity
n: number of animals
p.o.: oral administration
S.E.: standard error of the mean value
A: 8-[4,4-bis(4-fluorophenyl)-3-butenyl]-3,4-dimethyl-4-hydroxy-2-oxo-1-oxa-3,8-diazaspiro[4,5]decane hydrochloride
B: 3-benzyl-8-[4,4-bis(4-fluorophenyl)-3-butenyl]-4-hydroxy-4-methyl-2-oxo-1-oxa-3,8-diazaspiro[4,5]-decane hydrochloride

TABLE 1

| Compound | Inhibition of apomorphine-induced LMA | stereotypy as percentage of the control | Cataleptogenic effect $ED_{50}$ mg/kg p.o. | n |
|---|---|---|---|---|
| A | −40 | 0 | >300 | 5 |
| B | −25 | +15 | >300 | 5 |
| Clozapine | −25 | +11 | 31.9 | 5 |

Control
LMA: 100% (438.9 ± 54.7 sec ± S.E.)
Stereotypy: 100% (105.0 ± 13.7 sec ± S.E.)

It is obvious from Table 1 that a 2.5 mg/kg oral dose of the compounds of the formula (I) according to the invention decreased the apomorphine-induced locomotor hyperactivity with the same or a significantly higher efficiency than the reference drug did whereas, similarly to clozapine, they did not inhibit the stereotypy. Their cataleptogenic effect was at least ten times as favorable as that of the reference drug. Thus, it can be expected that the extrapyramidal side effects of the novel compounds of the formula (I) according to the invention would be less frequent or absent.

2. Inhibition of the hypoxic damage of the memory (nootropic effect)

Male, spontaneously (genetically) hypertensive rats weighing 210 to 230 g were used in these examinations. The active avoiding behavior was developed in a 6-channel automated Shuttle-box by a training consisting of 30 cycles during 3 days. Within a single cycle an intermittent light stimulus of 1 Hz frequency for 15 seconds as conditioned stimulus and an electric stimulus of 0.8 mA for 10 seconds as unconditioned stimulus were used with an intersignal time of 15 seconds.

On the 4th day, one hour before the experiment the animals were treated with a 10 mg/kg oral dose of the test compounds. Two control groups were used in these examinations, one of which was treated with placebo whereas the other one was treated with placebo and exposed to hypoxia. Piracetam (chemically 2-oxo-1-pyrrolidineacetic acid amide) and dihydroergotoxine were used as reference drugs. The performance of the animals was examined under hypoxic conditions in such a way that the boxes were flown through at a rate of 200 ml/min/box with a gaseous mixture containing 6% by volume of oxygen and 94% by volume of nitrogen. The number of the conditioned avoidance responses (as abbreviated hereinafter: CAR) was counted. The protective effect of the compounds against the hypoxic memory damage was calculated by using the following formula:

$$\text{protective effect \%} = \frac{(\text{treated } CAR\ \bar{x}) - (\text{placebo} + \text{hypoxia } CAR\ \bar{x})}{(\text{placebo } CAR\ \bar{x}) - (\text{placebo} + \text{hypoxia } CAR\ \bar{x})} \times 100$$

wherein
protective effect means the effect inhibiting the hypoxic memory damage expressed as percentage; and
CAR $\bar{x}$ means the average value of the number of conditioned responses in the animal group given.

The protective effect of the compounds against the hypoxic memory damage expressed as percentage of the control is shown in Table 2.

3. Inhibition of the hypobaric hypoxia

Male, spontaneously hypertensive rats weighing 200 to 220 g were used in these investigations. Groups consisting of 3 animals each were placed into a desiccator of 6 liters by volume, the pressure was decreased to 170 Hgmm (22.66 kPa) within 20 seconds and continuously maintained at the same level. One hour before the examination, the animals were treated with various oral doses of the test compounds. The $ED_{50}$ values (i.e. the doses prolonging the survival time of the test animals by 50% in comparison to that of the control group treated with placebo) were determined and summarized in Table 3.

The abbreviations used in the Table 2 and 3 are as follows:
C: 3-tert-butyl-8-[4,4-bis(4-fluorophenyl)-3-butenyl]-4-hydroxy-4-methyl-2-oxo-1-oxa-3,8-diazaspiro[4,5]decane hydrochloride
PIR: piracetam
DHE: dihydroergotoxine

TABLE 2

| Compound | Dose mg/kg p.o. | Protection against amnesia, % | n |
|---|---|---|---|
| C | 10 | 64 | 6 |
| PIR | 500 | 85 | 6 |
| DHE | 10 | 63 | 6 |

TABLE 3

| Compound | Protection against hypobaric hypoxia, ED$_{50}$ mg/kg p.o. | n |
|---|---|---|
| C | 23.7 | 10 |
| PIR | 293.0 | 10 |
| DHE | 50.0* | 10 |

*A survival of only 40% was achieved by the above high dose of DHE

4. Inhibition of the cerebral (brain) edema

The cerebral edema-inhibiting effect of the compounds was investigated by the following method [Ann. Pharm. Fr. 42, 431 (1984)].

A group consisting of 7 male Hannover-Wistar rats weighing 180 to 200 g were daily treated with 2.5 mg/kg of triethyl tin chloride (hereinafter TET) for 5 days to induce a cerebral edema. [TET (Merck-Schuchardt, Darmstadt, FRG) was dissolved in distilled water under stirring and the animals were orally treated with the stirred solution daily at 7 a.m.].

The reference and test compounds were homogenized in a 0.5% by weight carboxymethylcellulose solution by using an Ultra Turrax stirrer and the stirring was continued during the administration, too. These compounds were orally given first 1 hour, then 6 hours after the TET treatment in a volume of 0.5 ml/100 g of bodyweight in both cases. The control group received the solvent of TET (i.e. distilled water) and the carrier of the compounds (i.e. 0.5% by weight carboxymethylcellulose solution) at the same intervals and volumes as given above.

On the 5th day of treatments, 2 hours following the last administration of the test compound, the animals were decapitated, the whole brain was rapidly taken out, washed with cold, 0.9% by weight sodium chloride solution and the moisture was removed by filter paper. The wet weights of the brains were weighed with an accuracy of one tenth mg and placed onto an aluminum foil previously weighed. Subsequently, the brains were dried at 90° C. for 92 hours, then the total (gross) weight (i.e. the dry brain weight together with the weight of the aluminum foil) was determined. The water content of the brain and the change thereof, respectively, were calculated from the difference of the wet and dry brain weight. The change was expressed as percentage of the protection as follows:

$$\text{protection } \% = \frac{(TET - Ko) - (TET - V)}{(TET - Ko) - (Veh - Ko)}$$

wherein
(TET-Ko) means the mean water content (%) of the brain of animals treated with TET and carrier;
(TET-V) means the mean water content (%) of the brain of animals treated with TET and test compound;
(Veh-Ko) means the mean water content (%) of the brain of animals treated with distilled water and carrier.

The deviations of changes in the water content and dry weight of the brain were compared by using Student's "t" trial. Also here, piracetam and dihydroergotoxine were used as reference drugs. The results are summarized in Table 4.

Abbreviations used in Table 4 are as follows:
TET: triethyl tin chloride
dw: distilled water
Veh: vehicle (0.5% by weight carboxy methylcellulose solution)
D: 8-[4,4-bis(4-fluorophenyl)-3-butenyl]-3-[2-(3,4-dimethoxyphenyl)ethyl]-4-hydroxy-4-methyl-2-oxo-1-oxa-3,8-diazaspiro[4,5]decane maleate
E: 8-[4,4-bis(4-fluorophenyl)-3-butenyl]-4-hydroxy-4-methyl-2-oxo-1-oxa-3,8-diazaspiro[4,5]decane hydrochloride

TABLE 4

| Treatment | Dose/ umol/kg | Protection % |
|---|---|---|
| dw + Veh | — | — |
| TET + Veh | — | — |
| TET + compound C | 25 | 97.9 |
| TET + compound C | 50 | 102.0 |
| TET + compound C | 100 | 88.1 |
| TET + compound D | 100 | 102.2 |
| TET + compound E | 100 | 114.3 |
| TET + PIR | 100 | 16.7 |
| TET + DHE | 30* | 25.6 |

*DHE was administered in a dose of 30 mg/kg in the above experiment

Based on the above investigations, the compounds according to the invention are capable of effective protection from amnesia and memory damage due to hypoxia and of prolonging in low doses the survival time of the animals suffering from a severe hypoxia.

In the central nervous system a severe edema and increase in the brain water content as well as significant damages in the metabolizing activity of the brain are induced and the respiration of cells, the oxidative phosphorylation, oxidation of glutamate, succinate and glucose and the like are inhibited by triethyl tin chloride. These severe alterations are observed also in hypoxia and ischaemia; these primarily appear as the development of a cerebral edema and its sequels such as disturbances of the cognitive functions, dementia and the like. The compounds according to the invention ensured a complete protection from the development of a cerebral edema whereas no protective effect was achieved by the reference drugs.

The compounds according to the invention can be converted into pharmaceutical compositions. These compositions may be administered orally, rectally and-/or parenterally. For oral administration, the composition may be formulated e.g. as a tablet, dragée or capsule. In order to prepare oral compositions, e.g. lactose or starch may be used as carriers. Gelatine, carboxymethylcellulose sodium, methylcellulose, polyvinylpyrrolidone or starch gum are suitable binding or granulation agents. As disintegrating agents mainly potato starch or microcrystalline cellulose may be added though ultraamylopectin or formaldehyde-casein and the like are also useful. Talc, colloidal silicic acid, stearin, calcium or magnesium stearate and the like are suitable anti-adhesive and sliding agents. Liquid oral compositions can be formulated e.g. as suspensions, syrups or elixirs which may contain water, glycols, oils, alcohols as well as coloring and flavoring agents.

Tablets may be prepared e.g. by compression following wet granulation. The mixture of the active ingredient with the carriers and optionally with a part of the disintegrating additive is granulated with an aqueous, alcoholic or aqueous-alcoholic solution of the binding agents in a suitable equipment, then the granulate is dried. Subsequently, after mixing the other disintegrating, sliding and anti-adhesive additives to the dried granulate, the mixture is compressed to tablets. If desired, the tablets may be provided with a groove in order to facilitate the administration. Tablets may also directly be prepared from a mixture containing the active ingredient and suitable additives. The tablets may optionally be converted to dragée by employing commonly used pharmaceutical additives, e.g. protective, flavoring or coloring agents such as sugar, cellulose derivatives (methyl- or ethylcellulose, carboxymethylcellulose sodium and the like), polyvinylpyrrolidone, calcium phosphate, calcium carbonate, food dyes, dyeing lacquers, aromatizing agents, iron oxide, pigments and the like. Encapsulated compositions are prepared by filling a mixture of the active ingredient with the additives into capsules.

For rectal administration, the composition of the invention is formulated as a suppository containing a carrier mass, the so-called "adeps pro suppositorio" in addition to the active ingredient. As carriers, vegetable fats such as hardened vegetable oils, or triglycerides of $C_{12-18}$ fatty acids (preferably the carriers bearing the trade name Witepsol) may be used. The active ingredient is uniformly distributed in the molten carrier mass, then suppositories are prepared by moulding.

For parenteral administration, the composition of the invention is formulated as an injectable solution. For preparing these injectable solutions, the active ingredients are dissolved in distilled water and/or various organic solvents, e.g. glycol ethers, if desired, in the presence of solubilizing agents such as polyoxyethylene sorbitan monolaurate or monooleate or monostearate (Tween 20, Tween 60 or Tween 80), respectively. The injectable solution may further contain various auxiliary agents, e.g. preservatives such as ethylenediamine tetraacetate as well as pH-modifying and buffering substances or, if desired, a local anaesthetic agent such as lidocaine. Before filling into the ampoules, the injectable solution containing the composition of the invention is filtered and after filling in, it is subjected to sterilization.

The invention also relates to a method for treating the disturbances of the cognitive functions of mammals (including man). This method comprises administering a therapeutically effective amount of an active ingredient of the formula (I) or a pharmaceutically acceptable acid addition salt or quaternary ammonium salt thereof to the patient. Depending on the type and severity of the disease and conditions of the patient, the daily dose may vary between 0.1 and 40 mg/kg which may be administered daily once or in several subdoses in oral, rectal or parenteral route.

The invention is illustrated in detail by the aid of the following non-limiting Examples.

EXAMPLE 1

Preparation of
8-[3,3-bis(4-fluorophenyl)-2-propenyl]-4-hydroxy-4-methyl-2-oxo-3-n-propyl-1-oxa-3,8-diazaspiro[4,5]decane 9.3 g of 3,3-bis(4-fluorophenyl)-2-propenyl bromide dissolved in 50 ml of acetone are portionwise added to a mixture containing 6.85 g of 4-hydroxy-4-methyl-2-oxo-3-n-propyl-1-oxa-3,8-diazaspiro[4,5]decane and 4.2 g of anhydrous potassium carbonate in 68 ml of anhydrous acetone at room temperature during 1 hour while stirring, then the reaction mixture is stirred at room temperature for an additional 1 hour. After filtering off the inorganic salts and evaporating the solvent under reduced pressure, the residue is taken up in benzene, washed with water, dried over anhydrous sodium sulfate and then the solution is evaporated to one tenth its volume under reduced pressure. The product is precipitated by adding n-hexane to the evaporation residue. The crystals are filtered off and dried to give the title compound in 86% yield, m.p.: 128°-129° C.

Analysis: Calculated for $C_{26}H_{30}F_2N_2O_3$: C, 68.40; H, 6.62; F, 8.32; N, 6.14%; found: C, 68.44; H, 6.79; F, 8.50; N, 6.12%.

The hydrochloride salt is precipitated by adding ethereal hydrogen chloride solution to an ethereal solution of the base, m.p.: 233°-235° C.

The following compounds can analogously be prepared by using the appropriate starting substances.

8-(3,3-diphenyl-2-propenyl)-4-hydroxy-3-isopropyl-4-methyl-2-oxo-1-oxa-3,8-diazaspiro[4,5]decane hydrochloride, m.p.: 219°-221° C.;

8-[3,3-bis(4-fluorophenyl)-2-propenyl]-4-hydroxy-3-isopropyl-4-methyl-2-oxo-1-oxa-3,8-diazaspiro[4,5]decane hydrochloride, m.p.: 255°-260° C.

EXAMPLE 2

Preparation of
3-n-butyl-8-(3,3-diphenyl-2-propenyl)-4-hydroxy-4-methyl-2-oxo-1-oxa-3,8-diazaspiro[4,5]decane hydrochloride 92 ml of a hydrochloric acid solution of 3 mol/liter concentration are dropped to the solution of 5.2 g of 3-n-butyl-8-(3,3-diphenyl-2-propenyl)-4-methylene-2-oxo-1-oxa-3,8-diazaspiro[4,5]decane in 10.4 ml of 99% formic acid under stirring. Thereafter, the reaction mixture is stirred at 0° to 5° C. for 30 minutes. After filtering off, the crystalline precipitate is washed with water and dried to obtain the title product in 97% yield, m.p.: 104°-106° C.

Analysis of the base: Calculated for $C_{27}H_{34}N_2O_3$: C, 74.62; H, 7.89; N, 6.45%; found: C, 74.55; H, 8.01; N, 6.56%.

EXAMPLE 3

Preparation of
8-[4,4-bis(4-fluorophenyl)-3-butenyl]-4-hydroxy-3-isopropyl-4-methyl-2-oxo-1-oxa-3,8-diazaspiro[4,5]decane hydrochloride 11.3 g of 8-[4,4-bis(4-fluorophenyl)-3-butenyl]-3-isopropyl-4-methylene-2-oxo-1-oxa-3,8-diazaspiro[4,5]decane are stirred with 100 ml of 1 mol/liter hydrochloric acid at room temperature for 18 hours, then the crystalline precipitate is filtered off, washed with water, cooled to 5° C. and dried under reduced pressure to give the title hydrochloride in 96% yield, m.p.: 252°-255° C. (with decomposition).

The base is liberated from the hydrochloride by adding saturated aqueous sodium hydrogen carbonate solution, and extracted into chloroform. The organic layer is washed with water, dried over anhydrous magnesium sulfate and the solvent is distilled off under reduced pressure. After recrystallizing the residue from benzene, the title base is obtained in 87% yield, m.p.: 175°-176° C.

Analysis: Calculated for $C_{27}H_{32}F_2N_2O_3$ C, 68.91; H, 6.86; F, 8.08; N, 5.95%; found: C, 69.12; H, 6.94; F, 8.13; N, 6.10%.

EXAMPLE 4

Preparation of
8-(3,3-diphenyl-2-propenyl)-4-hydroxy-4-methyl-2-oxo-3-propyl-1-oxa-3,8-diazaspiro[4,5]decane hydrochloride A solution containing 12.6 g of 4-acetyl-1-(3,3-diphenyl-2-propenyl)-4-propylcarbamoyloxypiperidine and 0.4 g of sodium methoxide in 80 ml of methanol is refluxed under argon for 4 to 5 hours, then the solvent is evaporated under reduced pressure. The residue is stirred with 50 ml of 1.0 mol/liter hydrochloric acid at 0° to 5° C. for 15 minutes. After filtering off, the crystalline precipitate is washed with ice-cold water and dried to obtain the title hydrochloride in 82.4% yield, m.p.: 132°-134° C.

Analysis of the base: Calculated for $C_{26}H_{32}N_2O_3$: C, 74.25; H, 7.67; N, 6.66%; found: C, 74.40; H, 7.65; N, 6.53%.

EXAMPLE 5

Preparation of
8-[4,4-bis(4-fluorophenyl)-3-butenyl]-3-ethyl-4-hydroxy-4-methyl-2-oxo-1-oxa-3,8-diazaspiro[4,5]decane hydrochloride 7.0 g of 8-[4,4-bis(4-fluorophenyl)-3-butenyl]-3-ethyl-4-methylene-2-oxo-1-oxa-3,8-diazaspiro[4,5]decane are boiled with 320 ml of 0.1 mol/liter hydrochloric acid while stirring for 1 hour. After cooling down the reaction mixture to 5° C. and filtering it, the crystalline precipitate is washed with water and dried to obtain the title hydrochloride in 92.0% yield, m.p.: 238°-240° C. (with decomposition).

The base is liberated from the hydrochloride by adding aqueous sodium hydroxide solution.

Analysis of the base: Calculated for $C_{26}H_{30}F_2N_2O_3$: C, 68.40; H, 6.62; F, 8.32; N, 6.14%; found: C, 68.36; H, 6.68; F, 8.50; N, 6.25%.

EXAMPLE 6

Preparation of
8-[4,4-bis(4-fluorophenyl)-3-butenyl]-3-decyl-4-hydroxy-4-methyl-2-oxo-1-oxa-3,8-diazaspiro[4,5]decane hydrochloride 5.5 ml of decylamine are portionwise added to the solution of 10.3 g of 8-[4,4-bis(4-fluorophenyl)-3-butenyl]-4-methylene-2-oxo-1,3-dioxa-8-azaspiro[4,5]decane in 20 ml of benzene while stirring. The reaction is mildly exothermic and the temperature of the reaction mixture increases to 44°-45° C. After addition, the reaction mixture is stirred at room temperature for 18 to 20 hours. The crystalline precipitate is filtered off, washed with hexane and dried. The base is transformed to its hydrochloride by adding ethereal hydrogen chloride solution to obtain the title hydrochloride in 78.6% yield, m.p.: 140°-141° C.

Analysis of the base: Calculated for $C_{34}H_{46}F_2N_2O_3$: C, 71.80; H, 8.15; F, 6.68; N, 4.93%; found: C, 71.88; H, 8.33; F, 6.61; N, 5.11%.

The following compounds can analogously be prepared by using the appropriate starting substances.

8-[4,4-bis(4-fluorophenyl)-3-butenyl]-3-[2-(3,4-dimethoxyphenyl)ethyl]-4-hydroxy-4-methyl-2-oxo-1-oxa-3,8-diazaspiro[4,5]decane, m.p.: 143°-144° C.; the hydrogen maleate salt decomposes at 129°-132° C.;

8-[4,4-bis(4-fluorophenyl)-3-butenyl]-4-hydroxy-4-methyl-2-oxo-3-propyl-1-oxa-3,8-diazaspiro[4,5]decane hydrochloride, m.p.: 247°-250° C. (with decomposition);

8-[4,4-bis(4-fluorophenyl)-3-butenyl]-3-cyclohexyl-4-hydroxy-4-methyl-2-oxo-1-oxa-3,8-diazaspiro[4,5]decane hydrochloride, m.p: 256°-258° C. (with decomposition);

8-[3,3-bis(4-fluorophenyl)-2-propenyl]-3-butyl-4-hydroxy-4-methyl-2-oxo-1-oxa-3,8-diazaspiro[4,5]decane hydrochloride, m.p: 228°-230° C. (with decomposition);

3-benzyl-8-[4,4-bis(4-fluorophenyl)-3-butenyl]-4-hydroxy-4-methyl-2-oxo-1-oxa-3,8-diazaspiro[4,5]decane hydrochloride, m.p: 179°-181° C. (with decomposition);

8-[4,4-bis(4-fluorophenyl)-3-butenyl]-4-hydroxy-4-methyl-2-oxo-1-oxa-3,8-diazaspiro[4,5]decane hydrochloride, m.p: 155°-157° C. (with decomposition);

8-[4,4-bis(4-fluorophenyl)-3-butenyl]-4-hydroxy-4-methyl-3-(1-naphthyl)-2-oxo-1-oxa-3,8-diazaspiro[4,5]decane hydrochloride, m.p: 230°-233° C. (with decomposition);

3,4-dimethyl-8-(3,3-diphenyl-2-propenyl)-4-hydroxy-2-oxo-1-oxa-3,8-diazaspiro[4,5]decane hydrochloride, m.p: 211°-213° C. (with decomposition);

8-[4,4-bis(4-fluorophenyl)-3-butenyl]-3-tert-butyl-4-hydroxy-4-methyl-2-oxo-1-oxa-3,8-diazaspiro[4,5]decane hydrochloride, m.p: 220°-224° C. (with decomposition);

8-[3,3-bis(4-fluorophenyl)-2-propenyl]-3,4-dimethyl-4-hydroxy-2-oxo-1-oxa-3,8-diazaspiro[4,5]decane hydrochloride, m.p: 238°-240° C. (with decomposition);

8-[4,4-bis(4-fluorophenyl)-3-butenyl]-4-hydroxy-4-methyl-2-oxo-3-phenyl-1-oxa-3,8-diazaspiro[4,5]decane hydrochloride, m.p: 179°-181° C. (with decomposition);

8-[4,4-bis(4-fluorophenyl)-3-butenyl]-3,4-dimethyl-4-hydroxy-2-oxo-1-oxa-3,8-diazaspiro[4,5]decane, m.p: 144°-145° C.; the hydrochloride decomposes at 203°-204° C.;

8-[3,3-bis(3,5-dichlorophenyl)-2-propenyl]-3,4-dimethyl-4-hydroxy-2-oxo-1-oxa-3,8-diazaspiro[4,5]decane hydrochloride, m.p: 241°-244° C. (with decomposition); and 8-[4,4-bis(4-fluorophenyl)-3butenyl]-3-butyl-4-hydroxy-4-methyl-2-oxo-1-oxa-3,8-diazaspiro[4,5]decane hydrochloride, m.p: 229°-231° C. (with decomposition).

EXAMPLE 7

Preparation of
3-(4-chlorophenyl)-8-(3,3-diphenyl-2-propenyl)-4-hydroxy-4-methyl-2-oxo-1-oxa-3,8-diazaspiro[4,5]decane hydrochloride A solution containing 6.4 g of 4-acetyl-1-(3,3-diphenyl-2-propenyl)-4-hydroxypiperidine and 3.4 g of 4-chlorophenyl isocyanate in 30 ml of tripropylamine is gently refluxed under argon while stirring for 3 hours, then the solvent is distilled off under reduced pressure. After adding benzene to the evaporation residue, the insoluble materials are filtered off, the benzene solution is filtered through a silica gel layer and the solution is evaporated under reduced pressure. After recrystallizing the crude product from a mixture of ethanol and hexane under clarifying with activated carbon, the base obtained is converted to its hydrochloride salt by adding a solution of hydrogen in diisopropyl ether. The title hydrochloride is obtained in 47.3% yield, m.p.: 227°–230° C. (with decomposition).

Analysis of the base: Calculated for $C_{29}H_{29}ClN_2O_3$: C, 71.22; H, 5.98; Cl, 7.25; N, 5.73%; found: C, 71.29; H, 6.14; Cl, 7.40; N, 5.60%.

EXAMPLE 8

Preparation of 8-[4,4-bis(4-chlorophenyl)-3-butenyl]-3-butyl-4-hydroxy-4-methyl-2-oxo-1-oxa-3,8-diazaspiro[4,5]decane hydrochloride A mixture containing 7.27 g of 3-butyl-4-hydroxy-4-methyl-2-oxo-1-oxa-3,8-diazaspiro[4,5]decane, 12.89 g of 4,4-bis(4-chlorophenyl)-3-butenyl bromide, 4.98 g of anhydrous potassium carbonate and 0.6 g of potassium iodide in 73 ml of methyl isobutyl ketone is gently refluxed under argon while stirring for 6 hours. After cooling down, the inorganic salts are filtered off, washed with methyl isobutyl ketone, the filtrate is washed with water to neutral, dried over anhydrous magnesium sulfate and then the solvent is distilled off under reduced pressure. After recrystallizing the evaporation residue from ethanol, the product obtained is dissolved in ether and the hydrochloride is precipitated by adding ethereal hydrogen chloride solution to obtain 79.3% of the title hydrochloride, m.p.: 230°–233° C. (with decomposition).

Analysis of the base: Calculated for $C_{28}H_{34}Cl_2N_2O_3$: C, 64.89; H, 6.62; Cl, 13.70; N, 5.41%; found: C, 65.04; H, 6.66; Cl, 13.62; N, 5.48%.

EXAMPLE 9

Preparation of 8-[3,3-bis(4-fluorophenyl)-2-propenyl]-4-hydroxy-4-methyl-2-oxo-3-propyl-1-oxa-3,8-diazaspiro[4,5]decane-8-ium method iodide A mixture of 4.1 g of 8-[3,3-bis(4-fluorophenyl)-2-propenyl]-4-hydroxy-4-methyl-2-oxo-3-propyl-1-oxa-3,8-diazaspiro[4,5]decane and 0.7 ml of methyl iodide in 400 ml of methyl isobutyl ketone is refluxed for 2 hours. After cooling down, the crystalline precipitate is filtered off, washed with diisopropyl ether, cooled to 0° C. and dried to give 91.3% yield of the title quaternary ammonium salt, m.p.: 232°–233° C.

EXAMPLE 10

The new compounds according to the invention can be converted e.g. to the following pharmaceutical compositions.

(a) Preparation of tablets 50.0 g of active ingredient are mixed together with 92 g of lactose, 40 g of potato starch, 4 g of polyvinylpyrrolidine, 6 g of talc, 1 g of magnesium stearate, 1 g of colloidal silicon dioxide (Aerosil) and 6 g of ultraamylopectin and, after wet granulation, the product obtained is compressed to tablets containing 50 mg of the active ingredient each.

(b) Preparation of dragées

After coating the tablets prepared as described above in a known manner with a layer comprising sugar and talc, the dragées obtained are polished with a mixture of bee wax and carnauba wax to obtain dragées weighing 250 mg each.

(c) Preparation of capsules 100 g of active ingredient are thoroughly mixed together with 30 g of sodium lauryl sulfate, 280 g of starch, 280 g of lactose, 4 g of colloidal silicon dioxide (Aerosil) and 6 g of magnesium stearate, then the mixture is sieved and filled into hard gelatine capsules to obtain capsules containing 100 mg of active ingredient each.

(d) Preparation of suppositories (Note: all amounts are calculated for one suppository)

100.0 mg of active ingredient are thoroughly mixed together with 200.0 mg of lactose, 1700.0 mg of suppository base (e.g. Witepsol 4) are molten, cooled to 35° C. and the mixture of the active ingredient and lactose is mixed thereto by using a homogenizer. The product obtained is poured into cooled conic moulds. Each suppository weighes 2000 mg.

(e) Preparation of a suspension

| Components in 100 ml of the suspension: | |
| --- | --- |
| Active ingredient | 1.00 g |
| Sodium hydroxide | 0.26 g |
| Citric acid | 0.30 g |
| Nipagin (methyl 4-hydroxybenzoate sodium salt) | 0.10 g |
| Carbapol 940 (polyacrylic acid) | 0.30 g |
| 96% Ethanol | 1.00 g |
| Raspberry favor | 0.60 g |
| Sorbitol (Aqueous solution of 70%) | 71.00 g |
| Distilled water up to | 100.00 ml |

After adding Carbapol in little portions to the solution of Nipagin and citric acid in 20 ml of distilled water under vigorous stirring, the solution obtained is allowed to stand for 10 to 12 hours. Subsequently, the amount given above of sodium hydroxide dissolved in 1 ml of distilled water, the aqueous solution of sorbitol and finally the ethanolic solution of the raspberry favor are dropped in under stirring. The active ingredient is added in small portions to this mixture and suspended by using a submerged homogenizer. Finally, the suspension is supplemented to 100 ml by adding distilled water and the syrupy suspension is led through a colloid mill.

We claim:

1. A compound of the formula (I),

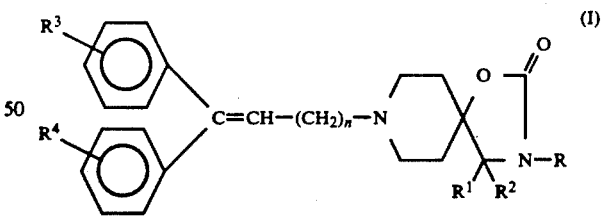

wherein

R means hydrogen, a $C_{1-12}$alkyl, $C_{3-6}$cycloalkyl, carbocyclic $C_{6-10}$aryl or carbocyclic $C_{6-10}$aryl-$C_{1-4}$alkyl group, the latter two unsubstituted or substituted on their aromatic moiety by at least one same or different halogen, $C_{1-4}$alkyl or $C_{1-4}$alkoxy group;

one of $R^1$ and $R^2$ stands for a hydroxyl group whereas the other means a methyl group;

$R^3$ and $R^4$, which are the same or different, represent hydrogen, or at least one halogen, $C_{1-4}$alkyl, $C_{1-4}$alkoxy, trihalomethyl group or a hydroxyl group free or esterified by a $C_{1-4}$alkanoic acid; and n is 1 or 2, or an isomer, solvate, hydrate, or a pharmaceutically acceptable acid addition or quaternary ammonium salt thereof.

2. A compound or pharmaceutically acceptable acid addition salt defined in claim 1 and selected from the group consisting of 8-{4,4-bis(4-fluorophenyl)-3-butenyl}-4-hydroxy-4-methyl-2-oxo-1-oxa-3,8-diazaspiro{4,5}decane or its hydrochloride, 8-{4,4-bis(4-fluorophenyl)-3-butenyl}-3,4-dimethyl-4-hydroxy-2-oxo-1-oxa-3,8-diazaspiro{4,5}decane or its hydrochloride, 8-{4,4-bis(4-fluorophenyl)-3-butenyl}-3-tert-butyl-4-hydroxy-4-methyl-2-oxo-1-oxa-3,8-diazaspiro{4,5}decane or its hydrochloride, 8-{4,4-bis(4-fluorophenyl)-3-butenyl}-3-butyl-4-hydroxy-4-methyl-2-oxo-1-oxa-3,8-diazaspiro{4,5}decane or its hydrochloride, 3-benzyl-8-{4,4-bis(4-fluorophenyl)-3-butenyl}-4-hydroxy-4-methyl-2-oxo-1-oxa-3,8-diazaspiro{4,5}decane or its hydrochloride, or an isomer, solvate, hydrate or other pharmaceutically acceptable acid addition or quaternary ammonium salts of these compounds.

3. 8-[4,4-bis(4-fluorophenyl)-3-butenyl]-3,4-dimethyl-4-hydroxy-2-oxo-1-oxa-3,8-diazaspiro[4,5] decane as defined in claim 1 or an isomer, solvate, hydrate or pharmaceutically acceptable acid addition or quaternary ammonium salt thereof.

4. 3-benzyl-8-[4,4-bis(4-fluorophenyl)-3-butenyl]-4-methyl-4-hydroxy-2-oxo-1-oxa-3,8-diazaspiro[4,5] decane as defined in claim 1 or an isomer, solvate, hydrate or pharmaceutically acceptable acid addition or quaternary ammonium salt thereof.

5. 8-[4,4-bis(4-fluorophenyl)-3-butenyl]-3-[2-(3,4-dimethoxyphenyl)ethyl]-4-hydroxy-4-methyl-2-oxo-1-oxa-3,8-diazaspiro-[4,5]decane as defined in claim 1 or an isomer, solvate, hydrate or pharmaceutically acceptable acid addition or quaternary ammonium salt thereof.

6. 8-[4,4-bis(4-fluorophenyl)-3-butenyl]-4-hydroxy-4-methyl-2-oxo-1-oxa-3,8-diazaspiro-[4,5]decane as defined in claim 1 or an isomer, solvate, hydrate or pharmaceutically acceptable acid addition or quaternary ammonium salt thereof.

7. 3-tert-butyl-8-{4,4-bis(4-fluorophenyl)-3-butenyl}-4-hydroxy-4-methyl-2-oxo-1-oxa-3,8-diazaspiro{4,5} decane as defined in claim 1 or an isomer, solvate, hydrate or pharmaceutically acceptable acid addition or quaternary ammonium salt thereof.

8. A pharmaceutical composition for treating amnesia and memory damage due to hypoxia, which comprises as active ingredient a therapeutically effective amount of the compound of the Formula I as defined in claim 1, or a pharmaceutically acceptable acid addition or quaternary ammonium salt thereof in admixture with a pharmaceutically acceptable inert carrier.

9. A method for the treatment of amnesia and memory damage due to hypoxia of a mammal which comprises administering to the mammal to be treated a therapeutically effective amount of a compound of the formula (I) as defined in claim 1, or a pharmaceutically acceptable acid addition or quaternary ammonium salt thereof alone or in the form of a pharmaceutical composition.

* * * * *